(12) United States Patent
Ploch et al.

(10) Patent No.: US 10,034,774 B2
(45) Date of Patent: Jul. 31, 2018

(54) DISPOSABLE MODULAR PATELLA PROTECTOR/CLAMP

(71) Applicants: Tyrone Ploch, Wenatchee, WA (US); Patrick Therien, Bothell, WA (US); Mark Broberg, East Wenatchee, WA (US)

(72) Inventors: Tyrone Ploch, Wenatchee, WA (US); Patrick Therien, Bothell, WA (US); Mark Broberg, East Wenatchee, WA (US)

( * ) Notice: Subject to any disclaimer, the term of this patent is extended or adjusted under 35 U.S.C. 154(b) by 508 days.

(21) Appl. No.: 14/221,150

(22) Filed: Mar. 20, 2014

(65) Prior Publication Data
US 2014/0288658 A1 Sep. 25, 2014

Related U.S. Application Data

(60) Provisional application No. 61/804,728, filed on Mar. 24, 2013.

(51) Int. Cl.
| | | |
|---|---|---|
| *A61F 2/46* | (2006.01) | |
| *A61B 17/92* | (2006.01) | |
| *A61B 17/88* | (2006.01) | |
| *A61B 90/57* | (2016.01) | |
| *B25B 7/02* | (2006.01) | |

(Continued)

(52) U.S. Cl.
CPC .......... *A61F 2/461* (2013.01); *A61B 17/8872* (2013.01); *A61B 17/92* (2013.01); *A61B 90/57* (2016.02); *A61F 2/46* (2013.01); *A61F 2/4603* (2013.01); *B25B 7/02* (2013.01); *B25B 7/06* (2013.01); *A61B 2017/0268* (2013.01); *A61B 2090/571* (2016.02); *A61F 2/3877* (2013.01); *A61F 2002/4622* (2013.01); *A61F 2002/4623* (2013.01); *A61F 2002/4624* (2013.01);
(Continued)

(58) Field of Classification Search
CPC ................ A61B 17/02; A61B 17/0206; A61B 2017/0268; A61B 17/8872; A61B 17/92; A61B 90/57; A61B 2090/571; A61F 2/3877; A61F 2/46; A61F 2/4603; A61F 2/461; A61F 2002/4622; A61F 2002/4623; A61F 2002/4624; A61F 2002/4631; B25B 7/02; B25B 7/06; Y10T 24/44376; Y10T 24/4444
See application file for complete search history.

(56) References Cited

U.S. PATENT DOCUMENTS

| | | | | |
|---|---|---|---|---|
| 717,526 A | * | 1/1903 | Barney | ................. B25B 27/205 81/302 |
| 4,616,634 A | * | 10/1986 | Vargas Garcia | ....... A61B 17/02 600/210 |

(Continued)

*Primary Examiner* — Larry E Waggle, Jr.
(74) *Attorney, Agent, or Firm* — James Haugen; Seattle Patnet Group LLC (57) ABSTRACT

A disposable modular patella protector and clamp is disclosed, providing the ability for a surgeon to shift the procedure sequence of the implantation of the patella from the end of a total knee replacement procedure to anytime during the procedure by providing a modular clamp that holds and protects the patella prosthesis and prepared patella. The clamp may be positioned in a manner in which it does not obstruct the patella or the prosthesis, allowing the surgeon to attend to other elements of the procedure while the bone cement is allowed to cure.

3 Claims, 7 Drawing Sheets

(51) Int. Cl.
    *B25B 7/06*         (2006.01)
    *A61B 17/02*      (2006.01)
    *A61F 2/38*       (2006.01)

(52) U.S. Cl.
    CPC . *A61F 2002/4631* (2013.01); *Y10T 24/44376* (2015.01); *Y10T 24/44444* (2015.01)

(56) References Cited

U.S. PATENT DOCUMENTS

| | | | | |
|---|---|---|---|---|
| 5,743,853 | A * | 4/1998 | Lauderdale | A61B 17/02 600/210 |
| 2006/0241633 | A1* | 10/2006 | Stalcup | A61B 17/025 606/86 R |
| 2012/0133163 | A1* | 5/2012 | Kavanagh | B25B 7/00 294/118 |
| 2013/0030539 | A1* | 1/2013 | Wright | A61B 17/1767 623/20.18 |
| 2013/0079787 | A1* | 3/2013 | Spencer Jones | A61B 17/1767 606/96 |

\* cited by examiner

DISPOSABLE MODULAR PATELLA PROTECTOR/CLAMP

FIELD

The instant application relates to a modular patella protector and clamp.

BACKGROUND

Total knee replacement procedures often require an orthopedic surgeon to bond a patella prosthesis to a patient's prepared patella using bone cement near the conclusion of the procedure. The patella prosthesis may be held in place during the time it takes the bonding cement to cure by a traditional non-modular medical instrument clamp, for example a scissor type, that maintains compression by being held by the hand or by being compressed then locked in position. Given that the bulky traditional clamp may interfere with the rest or the procedure, the orthopedic surgeon may have to wait and do nothing while the cement cures before completing the procedure. It may take up to ten minutes or longer for the cement to cure. In that situation, the total time for a full knee replacement may be extended, resulting in increased risk to the patent associated with being under anesthesia with an open wound, a constraint on the orthopedic surgeon's time and a waste of operating room resources.

SUMMARY

The instant application discloses, among other things, a disposable modular patella protector and clamp. The clamp may be used near the beginning of a full knee replacement procedure to compress a patella prosthesis on to the prepared patella bone, which may allow bonding of the two by way of a bone cement. The clamp may hold the patella prosthesis in place and may allow the cement to cure while the orthopedic surgeon concurrently performs that rest of the procedure. The clamp may also protect the prepared patella and patella prosthesis from damage from during the procedure. A clamp may be helpful in other procedures by allowing a patella to be moved or retracted out of the way and protected. A unique feature of the clamp allows placement of a matching retractor to further aid exposure.

The clamp may have one or more surfaces of sufficient size in contact with the prepared patella and the patella prosthesis. The contact surfaces may have one or more grip elements to securely engage the patella prosthesis and the prepared patella bone. The contact surfaces may be physically coupled by a connecting element that may produce an inwardly biased force between the contact surfaces, which may be sufficient to hold the clamp in place during the procedure. The design of the clamp may include a single sharp point of contact on the prepared patella bone surface and a circular soft interface with the prosthesis, which may allow free rotation while maintaining full compression. This may allow full rotational freedom and optimal placement of the clamp for best exposure. The clamp may be of a modular design and may be discarded at the conclusion of the procedure, or may be reused.

A separate applicator may be used to place and remove the clamp from the prepared patella and patella prosthesis. The contact surfaces of the clamp may have receiving ports to engage the applicator.

DESCRIPTION

In one implementation, a clamp may allow an orthopedic surgeon to compress a patella prosthesis onto a prepared patella with bone cement. The orthopedic surgeon may do the patella resection and implantation at any time during the procedure, apply the clamp, using an applicator, which may hold the prosthesis in place, and, while the bone cement is curing, tend to the rest of the procedure. The clamp may be sufficiently strong to remain in place with application of the compression while the rest of the procedure is completed. Once the procedure is completed, the clamp may be removed using an applicator. Use of the clamp may enable the surgeon to shift the implantation of the patella from the end of the procedure to any time during a procedure, resulting in a potential reduction in surgery time of ten minutes or more. This time savings may reduce operating room time and inefficiencies, and may reduce the time a patient is under anesthesia with an open wound.

The clamp may also have the added benefit of protecting the patella implant while the surgeon completes the joint arthroplasty, for example, from any loose instruments or saw blades with which it may come in contact.

The clamp may be of a modular design. The clamp may be designed to be applied with a specifically matching applicator device, modified traditional medical instruments, or unmodified traditional medical instruments. Once in place, the clamp may be disengaged from the applicator and left in its singular modular form. Once applied, the modular design of the clamp may result in a lower profile clamp, without the bulk of a traditional medical instrument clamp. A relatively small size of the clamp may offer the surgeon the space and capability to continue working on the procedure, while still acting as a prepared patella and patella prosthesis protector. The modular design may result in near universal compatibility with a variety of patients, as well as offering potentially lower manufacturing and shipping costs. The modular nature of the clamp may also allow it to be discarded at the end of the procedure.

Reference will now be made in detail to embodiments of the instant application, examples of which are illustrated in the accompanying drawings. Whenever possible, the same reference numbers will be used throughout the drawings to refer to the same or like parts.

Although discussed in reference to certain illustrations, the instant application is not limited to those illustrations.

Figure 1:
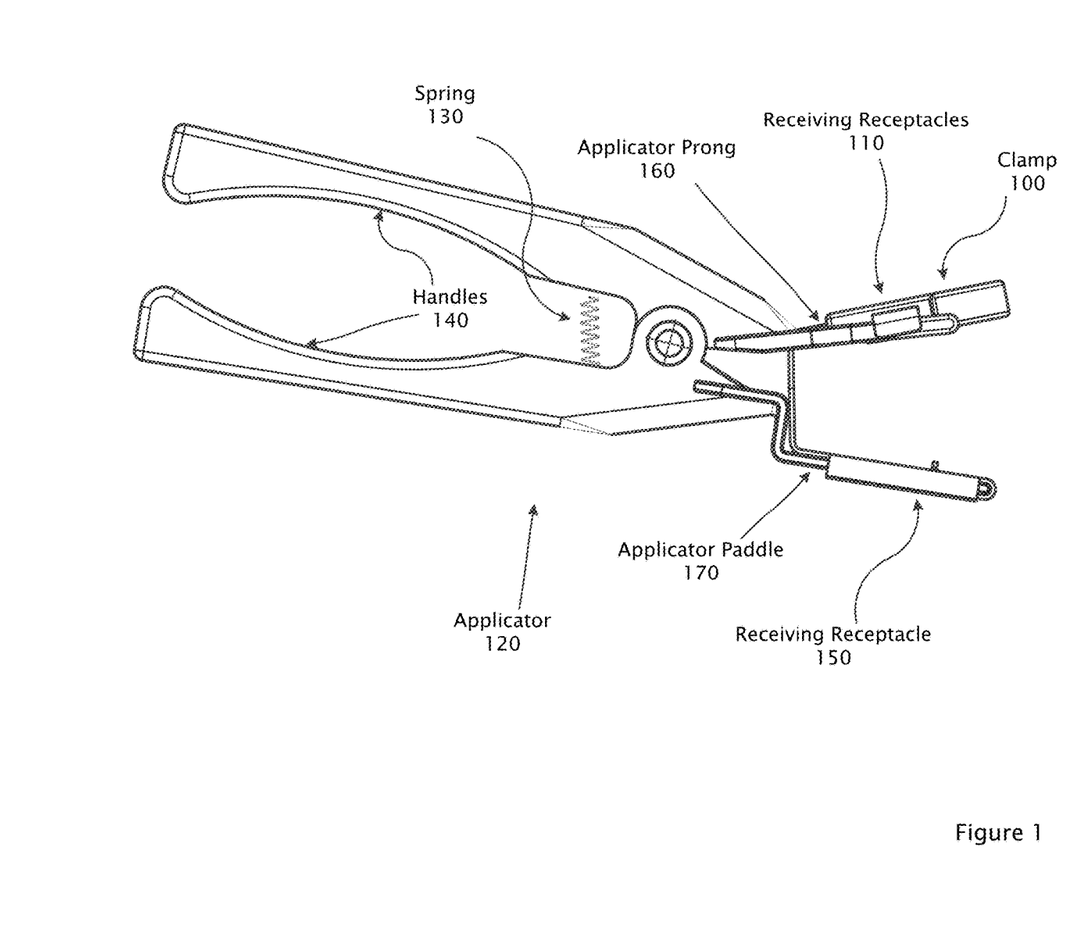
FIG. 1 is a side view of a clamp and applicator device according to one embodiment.

FIG. 1 is a side view of Clamp 100 and Applicator 120 according to one embodiment.

Clamp 100 may be used during, for example, knee replacement surgery, to secure a prosthesis to a patella, which may reduce time during the procedure by allowing a surgeon to work while bone cement hardens, for example.

Applicator Prong 160 may be tines, shaped to fit within Receiving Receptacles 110, which may be located on either side of a top of Clamp 100. Receiving Receptacles 110 may, for example, be cylindrical, and may encircle Applicator Prong 160, or may be a cylindrical section, configured to hold Applicator Prong 160 when pressure is applied. Applicator Paddle 170 may be paddle shaped to fit within Receiving Receptacle 150 on a bottom of Clamp 100, which may allow a user to squeeze Handles 140 of Applicator 120 together to spread Clamp 100, allowing the user to place Clamp 100 in a desired position. Handles 140 may have Spring 130 to spread them apart when Clamp 100 is not coupled to Applicator 120. One having skill in the art will recognize that various designs may be used to engage Applicator 120 with Clamp 100.

Figure 2:
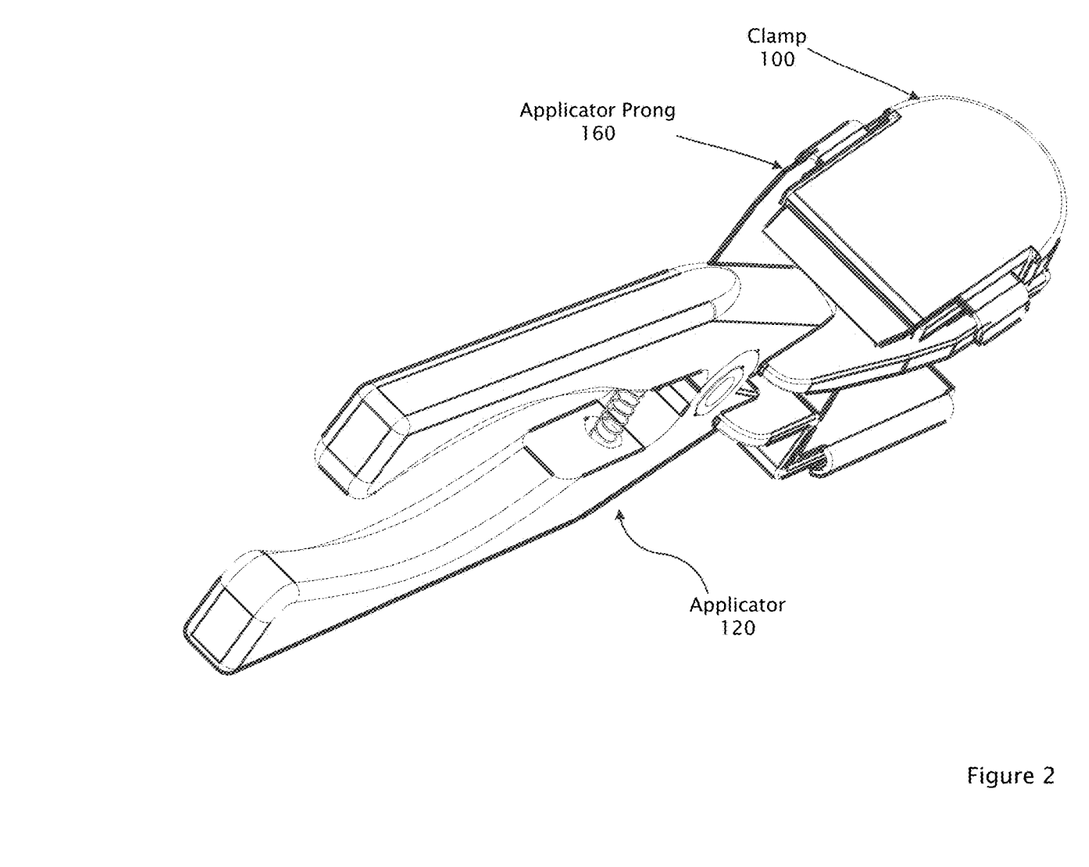
FIG. 2 is another view of a clamp and applicator device according to one embodiment.

FIG. 2 is another view of Clamp 100 and Applicator 120 according to one embodiment.

Figure 3:
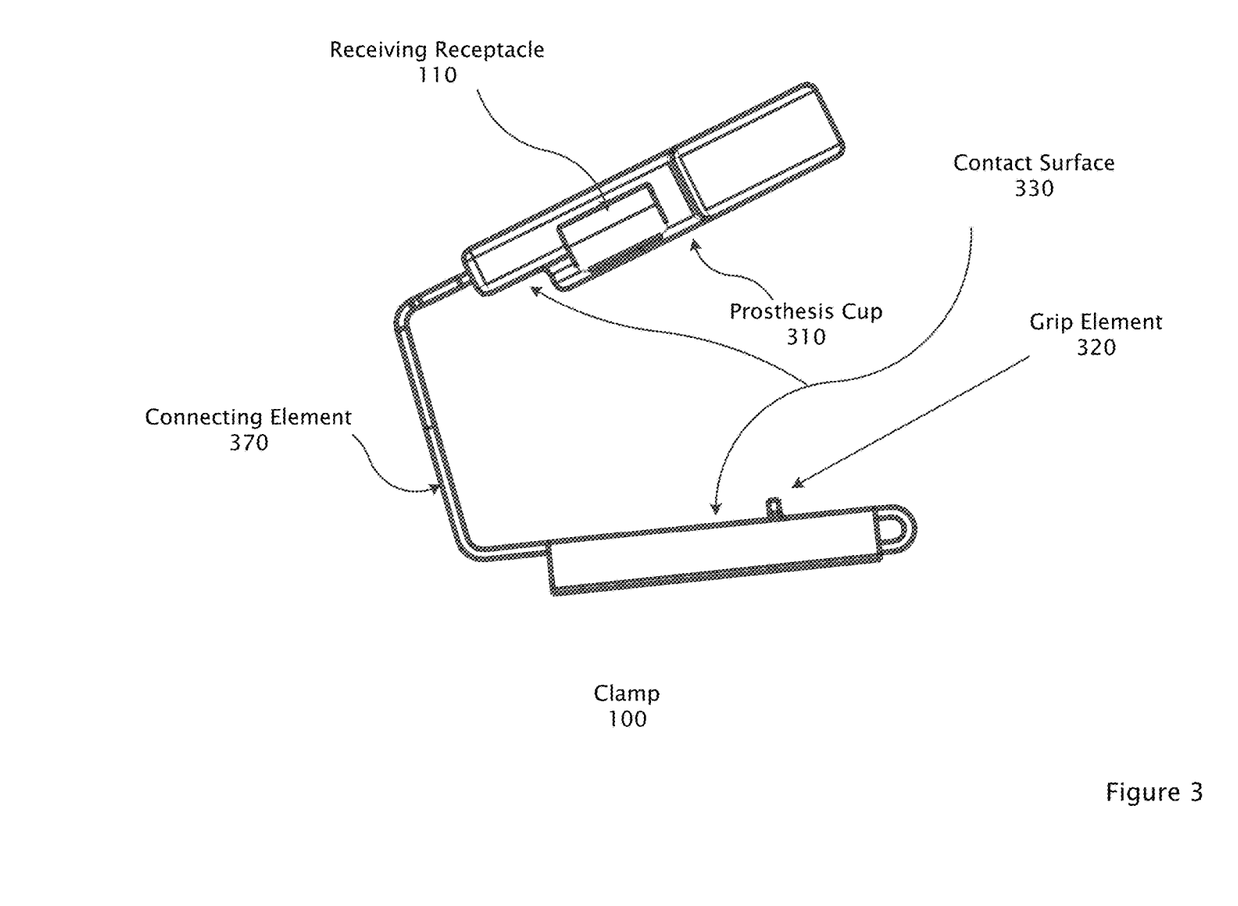
FIG. 3 is a side view of an open clamp according to one embodiment.

FIG. 3 is a side view of open Clamp 100 according to one embodiment. Prosthesis Cup 310 may be over-molded or may slip slip-on to Contact Surface 330. Prosthesis Cup 310 may be constructed of elastomer or other medical grade material or combination of materials that can securely engage a patella prosthesis, but not damage it.

Contact Surface 330 may be constructed of a medical grade material or combination of materials, including but not limited to, poly (methyl 2-methylpropenoate), commonly referred to as PMMA plastic. Two Contact Surfaces 330 may be coupled by Connecting Element 370. Connecting Element 370 may be constructed of a medical grade material including, but not limited to, stainless steel, such that Connecting Element 370 may produce an inwardly biased force between two Contact Surfaces 330 sufficient enough to hold the clamp in place during a procedure. Contact Surfaces 330 may include Grip Element 320 to securely engage the clamp to a prepared patella bone.

Figure 4:
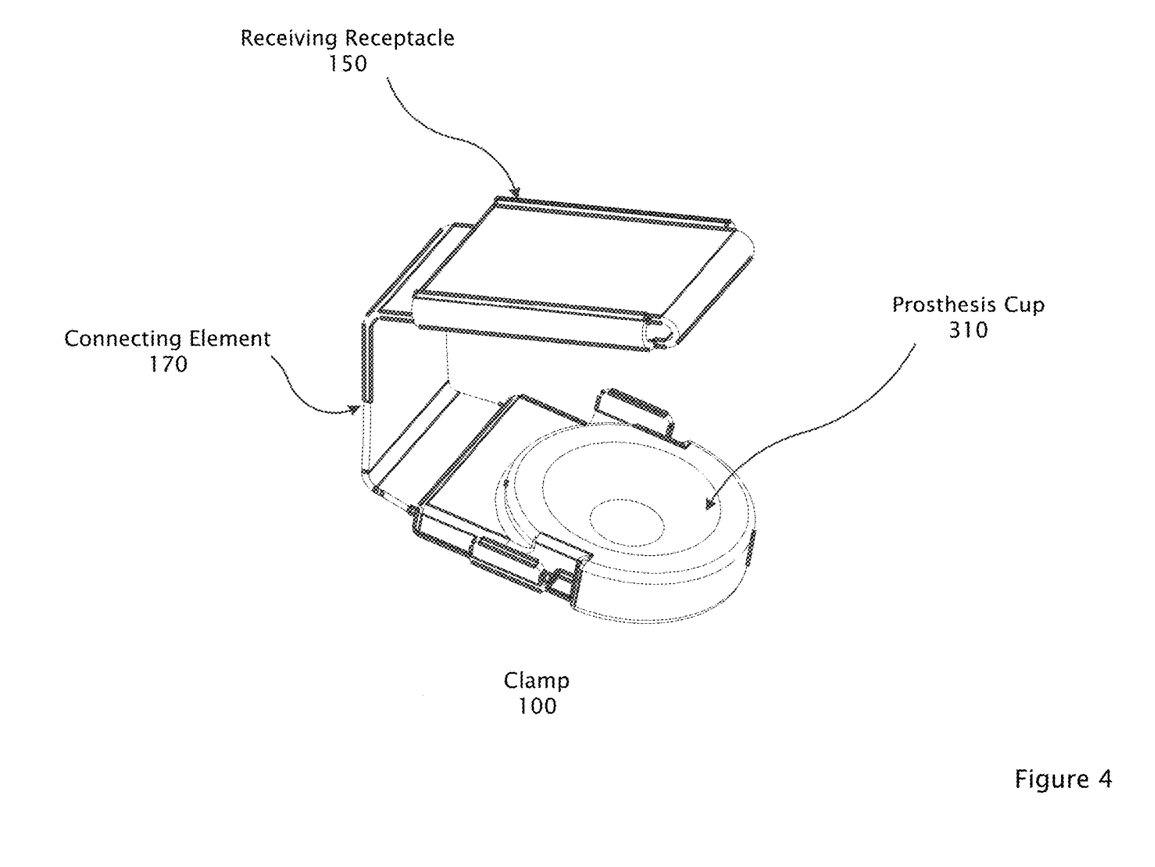
FIG. 4 is a bottom perspective view of an open clamp according to one embodiment.

FIG. 4 is a bottom perspective view of an open clamp according to one embodiment.

Figure 5:
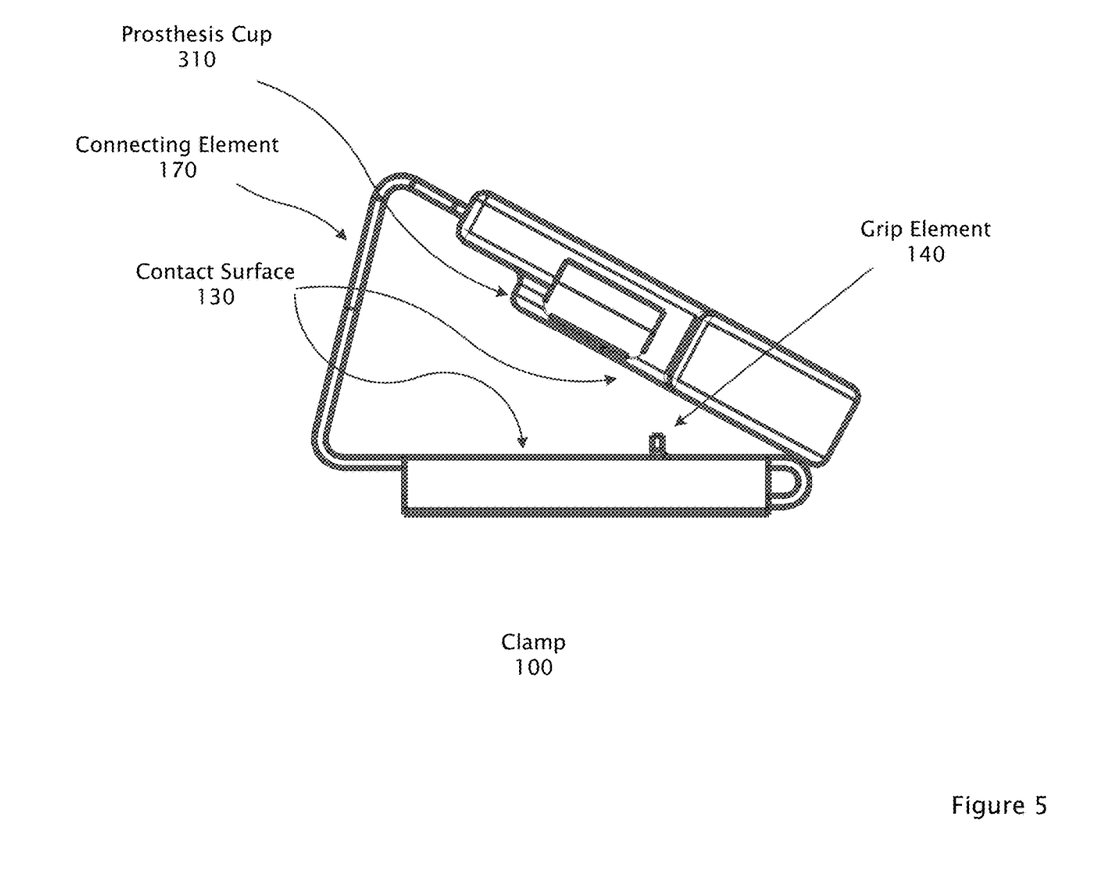
FIG. 5 is a side view of a closed clamp according to one embodiment.

FIG. 5 is a side view of a closed clamp according to one embodiment.

Figure 6:
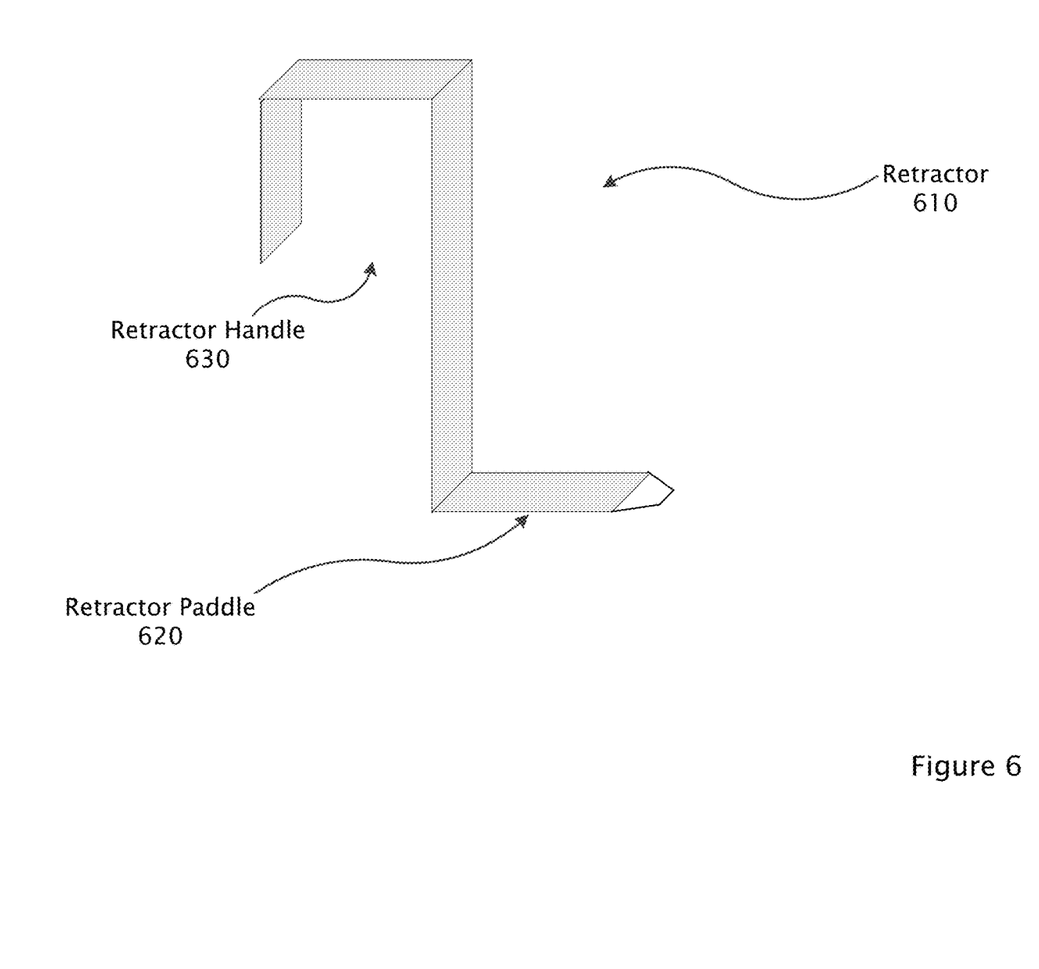
FIG. 6 is a perspective view of a retractor, according to one embodiment.

FIG. 6 is a perspective view of a retractor, according to one embodiment. Retractor 610 may be a metal strip pre-bent to a convenient shape. Retractor Paddle 620 may be inserted into Receiving Receptacle 150 on Clamp 100 while Clamp 100 is coupled to a patella. Retractor 610 may help protect the patella during an operation, and may be used to simplify removal of Clamp 100 when it is no longer desired. Retractor Handle 630 may act as a joystick to allow a surgeon to move or retract a clamp and may serve to aid the surgeon by allowing movement or retraction of a patella compressed within the clamp by the surgeon or an assistant during a procedure.

Figure 7:
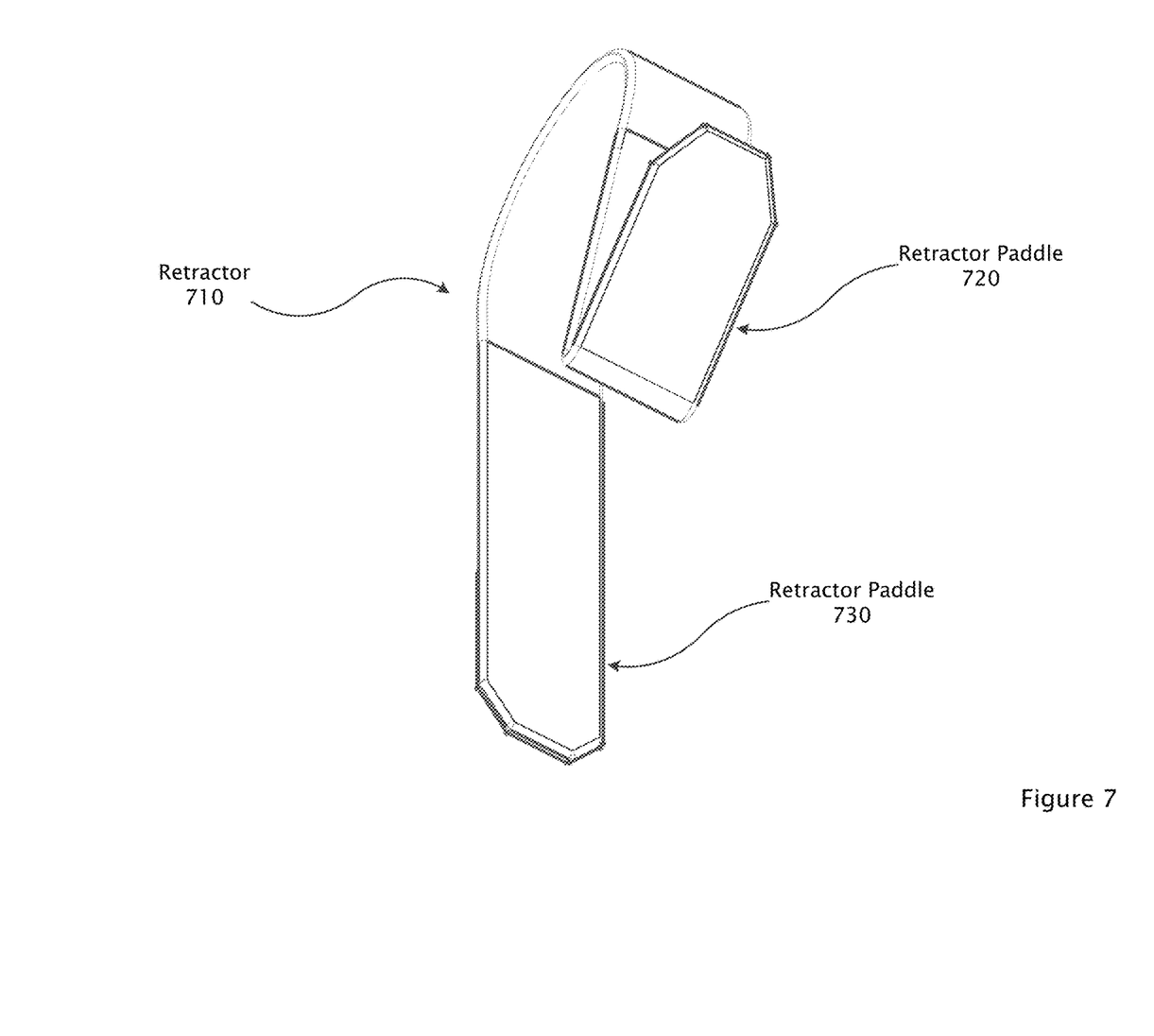
FIG. 7 is a perspective view of a retractor, according to another embodiment.

FIG. 7 is a perspective view of a retractor, according to another embodiment. Retractor 710 may be a metal strip pre-bent to a convenient shape. Either end of Retractor 710, Retractor Paddle 720 or 730, may be inserted into Receiving Receptacle 150 on Clamp 100 while Clamp 100 is coupled to a patella. Retractor 710 may help protect the patella during an operation, and may be used to simplify removal of Clamp 100 when it is no longer desired. Retractor 710 may act as a joystick to allow a surgeon to move or retract a clamp and may serve to aid the surgeon by allowing movement or retraction of a patella compressed within the clamp by the surgeon or an assistant during a procedure.

While the detailed description above has been expressed in terms of specific examples, those skilled in the art will appreciate that many other configurations could be used. Accordingly, it will be appreciated that various equivalent modifications of the above-described embodiments may be made without departing from the spirit and scope of the invention.

Additionally, the illustrated operations in the description show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel.

The foregoing description of various embodiments of the invention has been presented for the purposes of illustration and description. It is not intended to be exhaustive or to limit the invention to the precise form disclosed. It is intended that the scope of the invention be limited not by this detailed description, but rather by the claims appended hereto. The above specification, examples and data provide a complete description of the manufacture and use of the invention. Since many embodiments of the invention can be made without departing from the spirit and scope of the invention, the invention resides in the claims hereinafter appended.

The invention claimed is:

1. A clamp, comprising:
    a first surface, the first surface comprising a contact surface with one element to grip a prepared patella bone, operable to allow rotation of the clamp about the prepared patella bone;
    a second surface, comprising a contact surface coupled to a cup configured to receive a patella prosthesis;
    a first receiving receptacle, configured to receive a prong of an applicator;
    a second receiving receptacle, configured to receive a paddle of an applicator; and
    a connecting element coupling the first surface and the second surface, the connecting element providing a force pushing the first surface and second surface together.

2. The clamp of claim 1, wherein the connecting element comprises medical-grade stainless steel or other medical grade material with similar spring like characteristics.

3. The clamp of claim 1, wherein the cup comprises medical-grade elastomer.

* * * * *